United States Patent
Moshavegh et al.

(10) Patent No.: US 11,083,435 B2
(45) Date of Patent: Aug. 10, 2021

(54) SUPER RESOLUTION ULTRASOUND IMAGING

(71) Applicant: B-K MEDICAL APS, Herlev (DK)

(72) Inventors: Ramin Moshavegh, Gentofte (DK); Fredrik Gran, Limhamn (SE)

(73) Assignee: BK MEDICAL APS, Herlev (DK)

(*) Notice: Subject to any disclaimer, the term of this patent is extended or adjusted under 35 U.S.C. 154(b) by 196 days.

(21) Appl. No.: 16/250,538

(22) Filed: Jan. 17, 2019

(65) Prior Publication Data
US 2020/0229792 A1    Jul. 23, 2020

(51) Int. Cl.
| | |
|---|---|
| G06K 9/32 | (2006.01) |
| A61B 8/08 | (2006.01) |
| A61B 8/14 | (2006.01) |
| G06T 7/00 | (2017.01) |
| G01S 7/52 | (2006.01) |
| A61B 8/00 | (2006.01) |
| G06T 3/40 | (2006.01) |
| G01S 15/89 | (2006.01) |

(52) U.S. Cl.
CPC ............ *A61B 8/481* (2013.01); *A61B 8/085* (2013.01); *A61B 8/14* (2013.01); *A61B 8/5207* (2013.01); *A61B 8/0891* (2013.01); *A61B 8/4483* (2013.01); *G01S 7/52047* (2013.01); *G01S 15/8915* (2013.01); *G06T 3/4053* (2013.01); *G06T 7/0012* (2013.01)

(58) Field of Classification Search
USPC ................................ 382/130–134, 298, 299
See application file for complete search history.

(56) References Cited

U.S. PATENT DOCUMENTS

| | | | |
|---|---|---|---|
| 2012/0065494 A1* | 3/2012 | Gertner | A61B 5/489 600/411 |
| 2015/0272601 A1* | 10/2015 | Dixon | A61M 13/00 604/22 |
| 2020/0214673 A1* | 7/2020 | Yamamoto | A61B 8/463 |

OTHER PUBLICATIONS

Moshavegh, R. et al., Automated segmentation of free-lying cell nuclei in Pap smears for malignancy-associated change analysis, presented at 34th Annual International Conf.of the IEEE EMBS, San Diego, CA, USA Aug. 28-Sep. 1, 2012.

* cited by examiner

*Primary Examiner* — Suhail Khan
(74) *Attorney, Agent, or Firm* — Anthony M. Del Zoppo, III; Daugherty & Del Zoppo Co. LPA (57) ABSTRACT

An ultrasound imaging system includes a transducer array configured to transmit an ultrasound pressure field and receive an echo pressure field for a contrast-enhanced scan, and generate an electrical signal indicative of the received echo pressure field. The system further includes a signal processor configured to process the electrical signal and generate at least contrast enhanced ultrasound (CEUS) data indicative of nonlinear signal in the electrical signal. The system further includes a microbubble processor configured to process the CEUS data and generate microbubble data based on a predetermined contrast-agent microbubble size, shape and adjacency for microbubbles of interest. The system further includes a display configured to display a microbubble image indicative of the microbubble data.

19 Claims, 5 Drawing Sheets

SUPER RESOLUTION ULTRASOUND IMAGING

TECHNICAL FIELD

The following generally relates to ultrasound and more particularly to super resolution ultrasound imaging.

BACKGROUND

The resolution of an ultrasound imaging system is limited by diffraction to approximately half the wavelength of the sound employed. Such an imaging system is able to visualize organs and blood vessels. However, even high frequency ultrasound imaging systems fail to resolve microstructures and micro-vasculature. Super-resolution imaging of micro-vessels has been proposed in the literature. This technique may mitigate the diffraction limit, and, thus, provide a more precise and detailed visualization of vascular trees, which may enable the visualization of the micro-vasculature and the study of the perfusion of tissues and tumors. One approach includes tracking microbubbles by searching for the nearest neighbor (NN) detections in consecutive frames and merging them into a run. Unfortunately, this technique requires extensive artifact rejection, and, hence, increased processing and time requirements, to ensure that only microbubbles of interest are retained.

SUMMARY

Aspects of the application address the above matters, and others.

In one aspect, an ultrasound imaging system includes a transducer array configured to transmit an ultrasound pressure field and receive an echo pressure field for a contrast-enhanced scan, and generate an electrical signal indicative of the received echo pressure field. The system further includes a signal processor configured to process the electrical signal and generate at least contrast enhanced ultrasound (CEUS) data indicative of a nonlinear signal in the electrical signal. The system further includes a microbubble processor configured to process the CEUS data and generate microbubble data based on a predetermined contrast-agent microbubble size, shape and adjacency for microbubbles of interest. The system further includes a display configured to display a microbubble image indicative of the microbubble data.

In another aspect, a method includes acquiring an echo pressure field. The method further includes generating an electrical signal indicative of the acquired echo pressure field. The method further includes processing the electrical signal to generate at least contrast enhanced ultrasound (CEUS) data. The method further includes processing the CEUS data with a structuring element to generate microbubble data based on one or more predetermined contrast-agent microbubble sizes, shapes and adjacencies for microbubbles of interest.

In yet another aspect, a computer-readable storage medium storing instructions that when executed by a computer cause the computer to: acquire an echo pressure field; generate an electrical signal indicative of the acquired echo pressure field; process the electrical signal to generate at least CEUS data; and process the CEUS data with a structuring element to generate microbubble data based on one or more predetermined contrast-agent microbubble sizes, shapes and adjacencies for microbubbles of interest.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach for detecting only desired contrast agent microbubbles in contrast-enhanced ultrasound imaging without extensive artifact rejection, and, thus, reduces processing and time requirements relative to a configuration in which the approach described herein is not employed. In one instance, the approach makes use of a geometry of microbubbles to enable a full-control over a size and adjacency (spacing) of contrast agent microbubbles. This approach can increase a precision of free-lying microbubble detection and provides a feasible solution for real-time micro-vascular imaging on an ultrasound imaging system.

Figure 1:
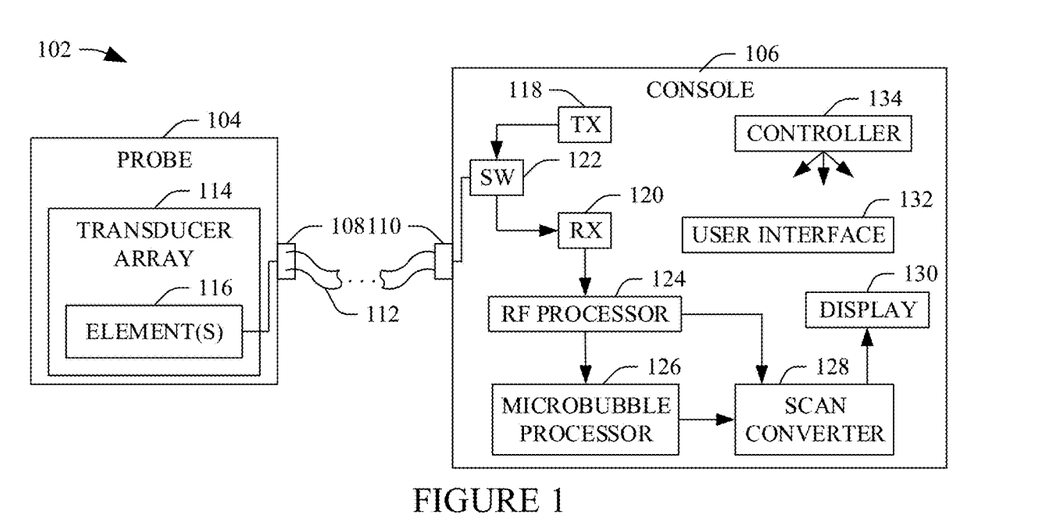
FIG. 1 diagrammatically illustrates an example ultrasound system in accordance with an embodiment(s) herein.

FIG. 1 illustrates an example imaging system 102 such as an ultrasound imaging system/scanner. The imaging system 102 includes a probe 104 and a console 106, which interface with each other through suitable complementary hardware (e.g., cable connectors 108 and 110 and a cable 112 as shown, etc.) and/or wireless interfaces (not visible).

The probe 104 includes a transducer array 114 with one or more transducer elements 116 (piezoelectric (PZT), capacitive micromachined ultrasound transducer (CMUT), etc.). The transducer array 114 includes a 1 or 2-D, linear, curved and/or otherwise shaped, fully populated or sparse, etc. array. The elements 116 are configured to convert excitation electrical pulses into an ultrasound pressure field and to convert a received ultrasound pressure field (an echo) into electrical (e.g., a radio frequency (RF)) signals. The received pressure field is produced in response to a transmitted pressure field interacting with matter, e.g., contrast agent microbubbles, red blood cells, tissue, etc.

The console 106 includes transmit circuitry (TX) 118 configured to generate the excitation electrical pulses and receive circuitry (RX) 120 configured to process the RF signals, e.g., amplify, digitize, and/or otherwise process the RF signals. The console 106 further includes a switch (SW) 122 configured to switch between the TX 118 and RX 120 for transmit and receive operations, e.g., by electrically connecting and electrically disconnecting the TX 118 and RX 120. In a variation, separate switches are utilized to switch between the TX 118 and RX 120.

The console 106 includes further an RF processor 124. In the illustrated embodiment, the RF processor 124 is configured to beamform (e.g., via delay-and-sum beamforming) the RF signals to construct a scanplane of scanlines of RF data. The RF signal processor 124 is further configured to detect the envelope of the scanlines beamform and log compress the detected envelope to generate envelope data. In one instance, the RF processor 124 is further configured perform other processing such as filtering, e.g., via a FIR filter, an IIR filter, and/or other processing.

For B-mode imaging, a single imaging sequence (pulse-echo) is utilized to detect linear signals from tissue. As utilized herein, the ultrasound data for the linear signals is referred to as tissue data. For contrast-enhanced imaging using a contrast agent with microbubbles (which is administered to a subject prior to and/or during the scan), the imaging sequence results in signals that are used to suppress the linear tissue signals and detect non-linear signals from the microbubbles. As utilized herein, the ultrasound data for the nonlinear signals is referred to as contrast enhanced ultrasound (CEUS) data.

A non-limiting example of a suitable contrast agent includes air microbubbles or gas-filled microbubbles. An example gas-filled microbubble contrast agent includes SONOVUE®, a product of Bracco Diagnostics Inc., with headquarters in NJ, USA. This contrast agent includes microbubbles with diameters in a range from 1 to 10 microns ($\mu m$). Other contrast agents and/or size of the microbubbles are also contemplated herein. In general, the gas in the microbubbles has a higher degree of echogenicity than cells, which results in increased contrast due to the echogenicity difference.

Examples of suitable contrast-enhanced imaging sequences include, but are not limited to, pulse inversion (PI), amplitude modulation (AM), and PIAM. These approaches utilize two transmission, where the second transmission is an inverted copy of the first transmission (i.e., PI), an amplitude modified version of the first transmission (i.e., AM), or both (i.e., PIAM), and the RF signals from the two transmission are combined to selectively cancel the linear response from tissue and amplify the nonlinear response from the contrast agents, yielding CEUS data.

Other contrast-enhanced imaging sequences are also contemplated herein. For example, with another approach three transmissions are used, in which two of them only half of the elements are used in transmit, and the third transmission uses all the elements. The RF signals for the transmissions with half the elements are then subtracted from the RF signal for the transmission with all the elements, yielding CEUS data, which highlights the position of the microbubbles.

The console 106 further includes a microbubble processor 126 configured to process a gray-scale representation of the CEUS data (e.g., the RF, the envelope, the compressed envelope, etc.) to generate a microbubble data. As described in greater detail below, the processor 126 employs an approach that automatically detects only signal corresponding to microbubbles satisfying a predetermined size (e.g., radius) and/or a predetermined adjacency (i.e. a spacing with a neighboring microbubbles). Also described in greater detail below, this approach can be used to enhance and/or segment vasculature.

In one instance, the approach described herein increases a sensitivity and a specificity of microbubble detection, e.g., relative to a configuration in which the microbubble processor 126 is omitted or not employed. This may allow for exploiting the full potential of super-resolution imaging for ultrasound micro-vasculature imaging. The approach includes control over the size and/or adjacency of microbubbles to be detected. The approach does not rely on an intensity of the microbubbles, but on a geometry and distribution of microbubbles, and ensures that overlapping and/or clustered microbubbles are not detected and only microbubbles with specific radii are detected.

It is to be appreciated that at least the RF processor 124 and the microbubble processor 126 can be implemented by a hardware processor (e.g., a central processing unit (CPU), graphics processing unit (GPU), a microprocessor, etc.) executing computer readable instructions encoded or embedded on computer readable storage medium, which excludes transitory medium.

The console 106 further includes a scan converter 128 and a display 130. The scan converter 128 is configured to scan convert the microbubble data and/or tissue data for display, e.g., by converting the microbubble data and/or tissue data to the coordinate system of the display 130. This may include changing the vertical and/or horizontal scan frequency of signal based on the display 130. Furthermore, the scan converter 128 can be configured to employ analog and/or digital scan converting techniques.

In one instance, the display 130 displays a user interface with an image region and displays a microbubble image in the image region. In another instance, the display 130 displays the microbubble image and a tissue image in different image regions of the user interface. In yet another instance, the display 130 displays the tissue image with the microbubble image superimposed thereover. In still another instance, the display 130 displays a combination of the foregoing display configurations.

The microbubble image can be displayed in real-time, i.e., as the echo signals are processed, and the microbubble data is generated. In one instance, this allows for dynamically tracking the microbubbles as they move, including tracking contrast agent uptake, peak contrast agent enhancement, and contrast agent wash out. Alternatively, or additionally, the visualization of the microbubbles is performed by using a persistence over time. For example, the visualization can be presented with an X second (X=1, 60, 300, 1000, etc. seconds) persistence in which frames of microbubbles accumulated over X seconds are displayed.

Figure 2:
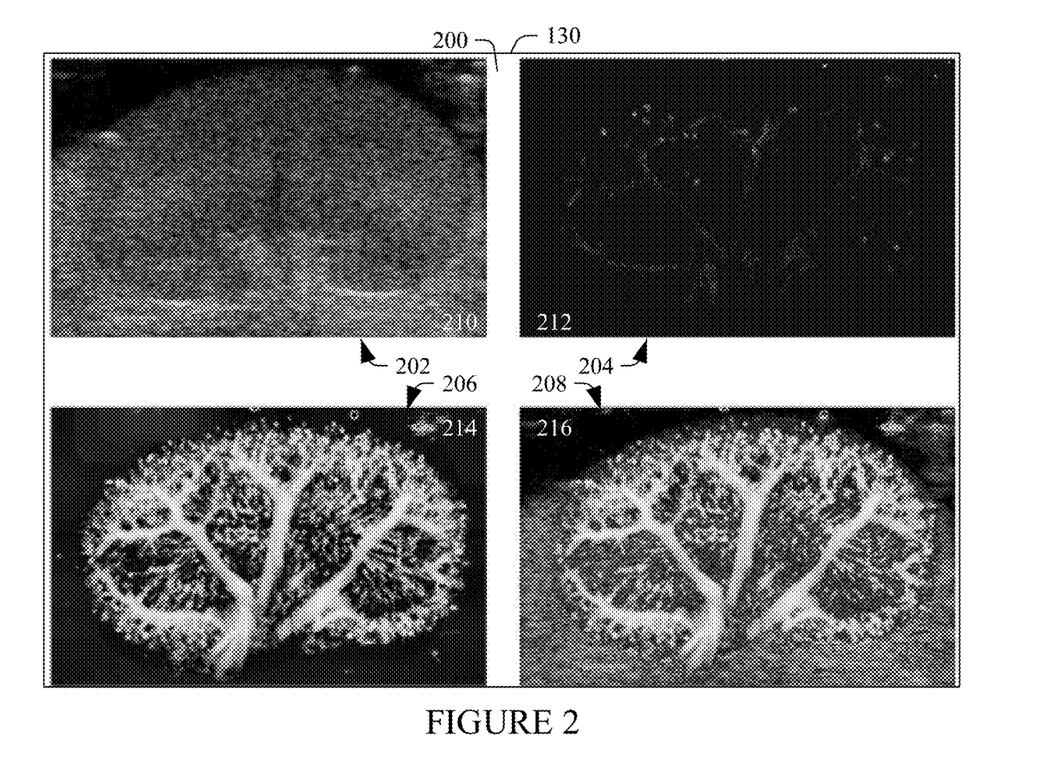
FIG. 2 diagrammatically illustrates an example display monitor image display configuration displaying images, in accordance with an embodiment(s) described herein.

Briefly turning to FIG. 2, example visualization is illustrated. In this example, the display 130 includes an example user interface 200 with image display regions 202, 204, 206 and 208. A B-mode image 210 is displayed in the display region 202, a microbubble image 212 with one second persistence is displayed in the display region 204, a microbubble image 214 with five-minute persistence is displayed in the display region 206, and a superposition image 216 with the microbubble image 214 superimposed over the B-mode image 210 is displayed in the display region 208. In a variation, one or more of the display regions 202, 204, 206 and 208 is omitted.

Returning to FIG. 1, the console 106 further includes a user interface 132, which includes one or more input devices (e.g., a button, a touch pad, a touch screen, etc.) and one or more output devices (e.g., a display screen, a speaker, etc.). The console 106 further includes a controller 134 configured to control one or more of the transmit circuitry 118, the receive circuitry 120, the switch 122, the RF processor 124, the microbubble processor 126, the scan converter 128, the display 130, and/or the user interface 132.

Figure 3:
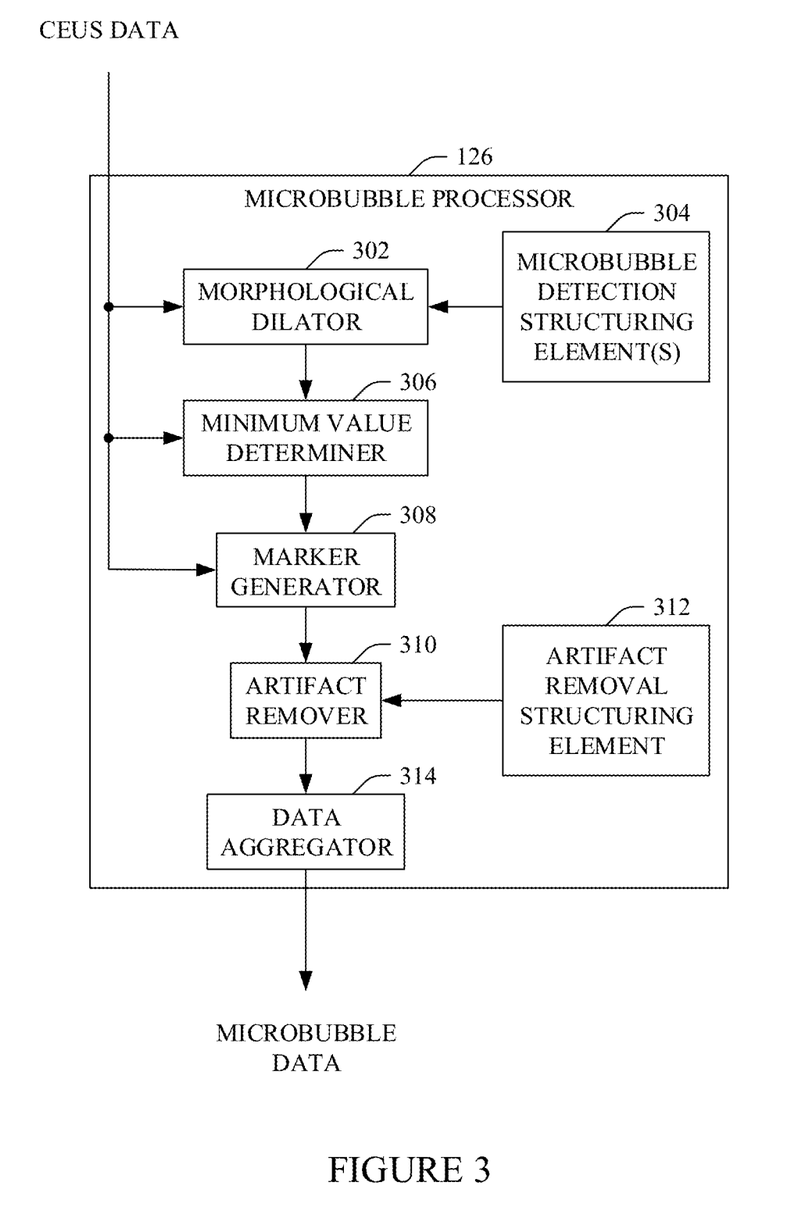
FIG. 3 diagrammatically illustrates an example microbubble processor, in accordance with an embodiment(s) described herein.

FIG. 3 diagrammatically illustrates a non-limiting example of the microbubble processor 126. The microbubble processor 126 receives, as an input, the CEUS data, and provides, as an output, microbubble data.

The microbubble processor 126 includes a morphological dilator 302 that dilates residual structures represented in the CEUS data based on one or more of a microbubble detection structuring element 304. In general, the microbubble detection structuring element 304 can be 1-D, 2-D or 3-D, square, rectangular, circular, elliptical and/or other shape, etc. In this example, the microbubble detection structuring element 304 is a ring-shaped object (i.e. an annular structuring element), since microbubbles are generally circular structures, that defines a maximum size (i.e. radius or diameter) of a microbubble of interest and a minimum adjacency (i.e. spacing between the microbubble of interest and each neighboring microbubble). In other examples, another shape(s) can be utilized.

The morphological dilator 302 evaluates each structure represented in the CEUS data with the microbubble detection structuring element 304. Where both criteria are not satisfied, the structure is dilated based on (e.g., up to) the size. However, where both criteria are satisfied, a bright spot from a center region of the structure is removed (e.g., the pixel value(s) representing the centroid is set to zero) due to dilation. The removed bright spots identify the locations of microbubbles of interest. In general, each structure, after dilation, will look like a ring and lack a centroid where the structure meets both criteria or a disk and retain its centroid where the structure does not meet both criteria.

The microbubble processor 126 further includes a minimum value determiner 306. The minimum value determiner 306 computes a value for a coordinate (x,y) as a minimum of a value at that coordinate (x,y) in the CEUS date and a value at that coordinate (x,y) in the dilated data. For example, with binary values, where the value is 1 in one of the data sets and 0 in the other of the data set or 0 in both data sets, the value at the coordinate (x,y) is set to 0, and where the value at the coordinate (x,y) is 1 in both of the data sets, the value at the coordinate (x,y) is set to 1. For a gray scale image, the value at the coordinate (x,y) is set to the minimum gray scale value.

The microbubble processor 126 further includes a marker generator 308. The marker generator 308 determines an arithmetic difference between the value at the coordinate (x,y) of the CEUS data and a value at that coordinate (x,y) of the minimum value data for all coordinates in the data. In general, the resulting difference data includes markers that correspond only to the structures satisfying both criteria, and not markers for structures that did not satisfy both criteria. The markers in the difference data represents the positions of the microbubbles of interest in the CEUS data.

The illustrated microbubble processor 126 further includes an artifact remover 310 configured to remove any artifact in the foreground. In one instance, this is achieved by first morphologically eroding the difference data with an artifact removal (e.g., a disc) structuring element 312 having a pre-determined size and then dilating the eroded difference data with the artifact removal structuring element 312. The artifact removal structuring element 312 has a size that is smaller than the size of the microbubble detection structuring element 304. For example, where a minimum size of the microbubble detection structuring element 304 is 1 micron, the artifact removal structuring element 312 is less than 1 micron, e.g., 0.1, 0.2, 0.5, 0.9, etc. microns. In a variation, the artifact remover 310 and artifact removal structuring element 312 are omitted.

The illustrated microbubble processor 126 further includes a data aggregator 314 configured to aggregate difference data (or artifact removed difference data) for different size microbubble detection structuring elements 304, where the input CEUS data is processed with more than one microbubble detection structuring element 304 (e.g., ranging from 1 micron or less to 20 microns or more or less), to produce a microbubble data. The number of different microbubble detection structuring elements 304 is based on a default, a user preference, input parameters (e.g., first and last inner and/or outer radii and predetermined or input incremental values of the inner and/or out radii), and/or otherwise. In one instance, the output microbubble data includes the markers from all of different microbubble data. In another variation, the data aggregator 314 is omitted or by-passed, e.g., where the input CEUS data is processed only once.

The following is non-limiting pseudo-code for determining the output microbubble data. For this example, "env" represents the CEUS data, B represents an annular structuring element, λ represents microbubble radius, $r_1$ represents a first radius of the annular structuring element B, $r_2$ represents a last radius of annular structuring element B, α represents microbubble adjacency (spacing between microbubbles), ⊕ represents morphological dilation, ⊖ represents morphological erosion, $B_0$ represents a disc structuring element, $\lambda_0$ represents a radius of the disc structuring element $B_0$, g represents marker data for a given $\lambda_i$ and $\alpha_i$ computed from $\Psi_{anopen}$(env, B)−env where $\Psi_{anopen}$(env, B) is a morphological annular opening operation and is given by (env⊕B)∧env and where ∧ denotes point-wise minimum, and ∪ is the union operator.

---
Algorithm 1 Free-lying microbubble detection
---

Input: 2-D Envelope data env, and parameters $\lambda_0$, $\alpha$, $r_1$, and $r_2$.
Output: Binary mask $B_{MBs}$ containing a marker for each free-lying microbubble objects detected
 1: procedure MB detection
 2:    Let $B_0$ be a disk structuring element of radius $\lambda_0$
 3:    for each $\lambda = r_1$ to $r_2$ do
 4:        Let B be an annular structuring element with inner and outer radii of $\lambda$ and $\lambda + \alpha$ respectively
 5:        $g = \psi_{anopen}(env, B) - env$
 6:        $X_1 = g > 0$
 7:        $X_2 = (X_1 \ominus B_0) \oplus B_0$
 8:        $X = X \cup X_2$
 9:    end for
10:    $B_{MBs}$ = set of centroids of the connected components in X
11: end procedure Note:
$\oplus$ and $\ominus$ denote morphological dilation and erosion respectively.

In one instance, $\lambda$ is used to retain only those microbubbles with a given size and remove all microbubbles outside of the given size. In another instance, $\alpha$ is used to retain only those microbubbles with a given spacing and remove all microbubbles that fail the spacing, e.g., overlapping microbubbles and/or clustered microbubbles. In yet another instance, $\lambda$ and $\alpha$ are used in combination to retain only those microbubbles with the given size and the given spacing. Where the CEUS data is processed only once, $r_2$ equals $r_1$. Where the artifact remover 310 is omitted or by-passed, steps 2 and 7 are omitted, and $X=X\cup X_1$ in step 8.

FIGS. 4, 5, 6, 7, 8, 9, 10, 11 and 12 illustrate a non-limiting example in which two different microbubble detection structuring elements 304 are employed.

Figure 4:
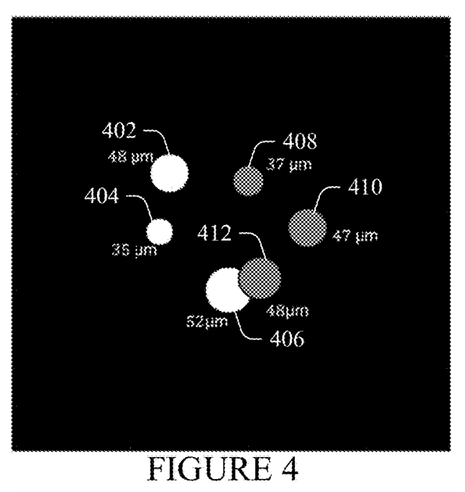
FIG. 4 graphically illustrates a simulated CEUS image of microbubbles, in accordance with an embodiment(s) described herein.

FIG. 4 illustrates input simulated CEUS data that includes a plurality of circular structures 402, 404, 406, 408, 410 and 412. The circular structure 402 has a radius of 48 microns, the circular structure 404 has a radius of 35 microns, the circular structure 406 has a radius of 52 microns, the circular structure 408 has a radius of 37 microns, the circular structure 410 has a radius of 47 microns, and the circular structure 412 has a radius of 48 microns. Circular structures 406 and 412 partially overlap.

Figure 5:
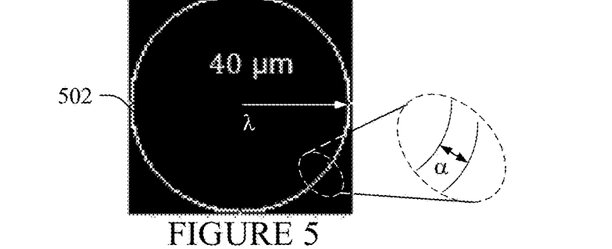
FIG. 5 graphically illustrates an example annular structuring element, in accordance with an embodiment(s) described herein.

FIG. 5 illustrates a microbubble detection structuring element 502 with a radius $\lambda$ of 40 microns (which defines a maximum size of a microbubble) and an adjacency $\alpha$ of zero (which defines a minimum spacing between microbubbles) which excludes only those microbubbles that overlap. FIG. 5 shows $\alpha$ greater than zero only for explanatory purposes and the skilled artisan would understand that where $\alpha$ equals zero, the illustrated portion of the microbubble detection structuring element 502 and the adjacency portion shown a away would lie on top of each other.

Figure 6:
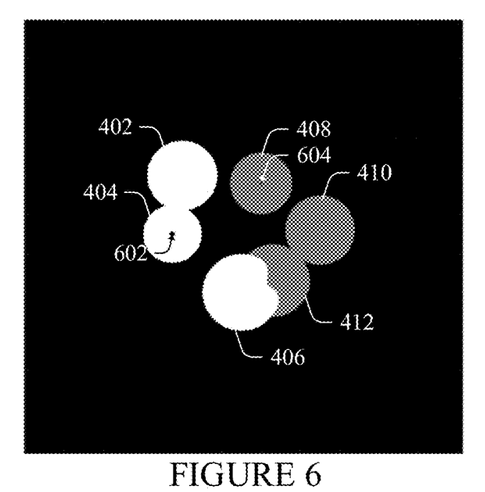
FIG. 6 graphically illustrates morphologically dilated data, in accordance with an embodiment(s) described herein.

FIG. 6 shows results of gray-scale morphological dilation of a simulated received CEUS data with the microbubble detection structuring element 502. Each of the circular structures 402, 404, 406, 408, 410 and 412 has been dilated by the size of the microbubble detection structuring element and only those circular structures with a radius equal to or less than the radius $\lambda$ of 47 microns and with no overlapping with neighboring structure have their centroid removed. In particular, the circular structures 402, 406, 410 and 412 have radii greater than 40 microns and structures 406 and 412 overlap so their centroids remain. However, the structures 404 and 408 have radii less than 40 microns and do not overlap other structures so their centroids are removed, as shown by the black regions 602 and 604 respectively in the structures 404 and 408.

Figure 7:
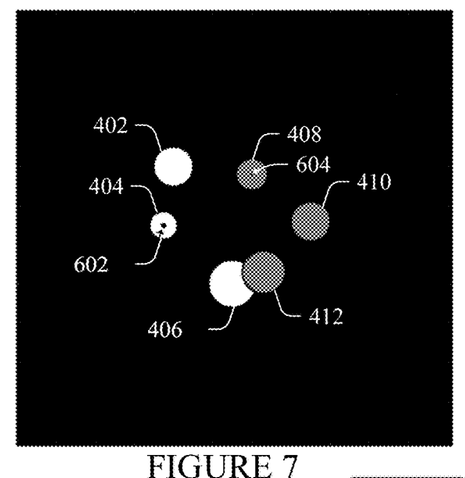
FIG. 7 graphically illustrates difference data, in accordance with an embodiment(s) described herein.

FIG. 7 shows results of identifying a point-wise minimum of same coordinate (x,y (or x,y,z)) in the simulated received CEUS data (FIG. 4) and the dilated data (FIG. 6). As described herein, for this step, a value of the coordinate (x,y) is a minimum of the values of that coordinate (x,y) from the CEUS data and dilated data. That is, for a given coordinate (x,y), where at least one of the value of the CEUS data or the value of the dilated data is black, the coordinate (x,y) is set to black, and where both the value of the CEUS and the value of the dilated data is not black (e.g., white or gray in this example), the coordinate (x,y) is set to white or gray. As shown, the circular structures 402, 404, 406, 408, 410 and 412 are returned to approximately their original radii.

Figure 8:
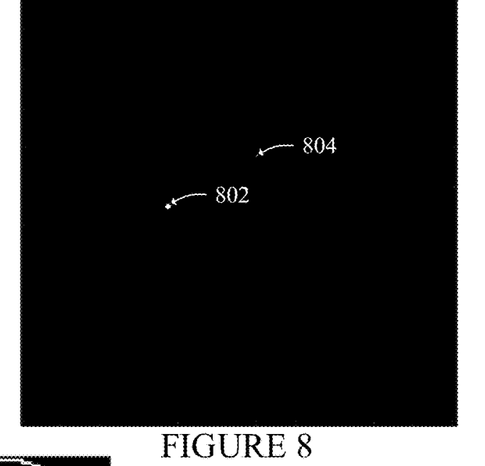
FIG. 8 graphically illustrates microbubble data (markers locating candidate microbubbles), in accordance with an embodiment(s) described herein.

FIG. 8 shows microbubble data created by calculating the arithmetic difference between each coordinate (x,y, or x,y,z) in the simulated CEUS data (FIG. 4) and the minimum value data (FIG. 7). As shown, only the markers 802 and 804 corresponding to the centroids of the structures 404 and 408 remain. Generally, since the size of the structures in the CEUS image (FIG. 4) and the minimum value data (FIG. 7) is approximately the same, with the only difference being the structures 404 and 408 in the minimum value data do not have their centroids, the difference between this data yields the centroids of the structures 404 and 408 as the markers 802 and 804. Again, the markers 802 and 804 indicate the position of the microbubbles of interest.

Figure 9:
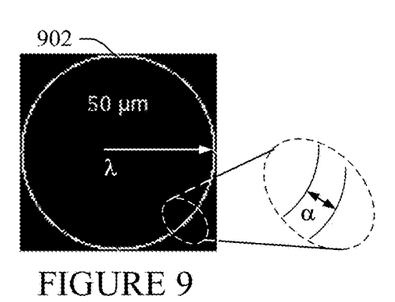
FIG. 9 graphically illustrates another example of annular structuring element, in accordance with an embodiment(s) described herein.

FIG. 9 illustrates a microbubble detection structuring element 902 with a radius $\lambda$ of 50 microns (which defines a maximum size of a microbubble) and an adjacency $\alpha$ of zero (which defines a minimum spacing between microbubbles) which excludes only those microbubbles that overlap. FIG. 9 shows $\alpha$ greater than zero only for explanatory purposes and the skilled artisan would understand that where $\alpha$ equals zero, the illustrated portion of the microbubble detection structuring element 902 and the adjacency portion shown a away would lie on top of each other.

Figure 10:
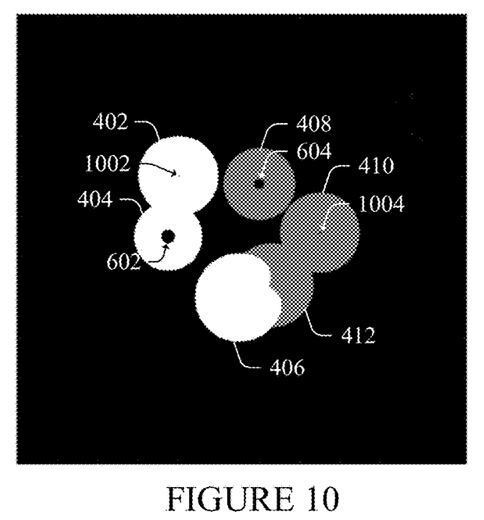
FIG. 10 graphically illustrates morphologically dilated data, in accordance with an embodiment(s) described herein.

FIG. 10 shows results of processing the simulated received CEUS data with the microbubble detection structuring element 902. Each of the circular structures 402, 404, 406, 408, 410 and 412 of FIG. 4 has been dilated by the microbubble detection structuring element 902 and only those circular structures with a radius equal to or less than the radius $\lambda$ of 50 microns and with no overlapping with neighboring structure have their centroid removed. In particular, the circular structures 406 and 412 have radii greater than 50 microns and structures 406 and 412 overlap so their centroids are not removed. However, the structures 402, 404, 408 and 410 have radii less than 50 microns and do not overlap other structures so their centroids are removed, as shown by the black regions 602, 604, 1002 and 1004 respectively in the structures 402, 404, 408 and 410.

Figure 11:
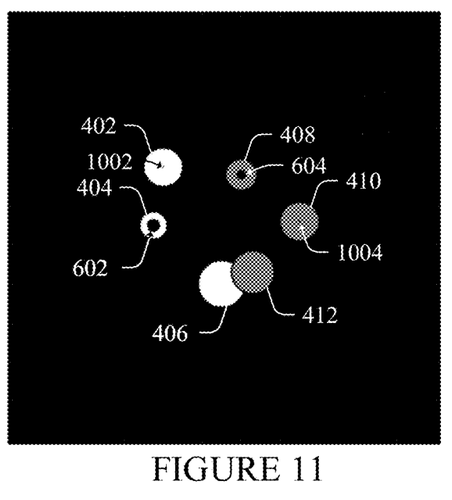
FIG. 11 graphically illustrates difference data, in accordance with an embodiment(s) described herein.

FIG. 11 shows results of identifying a point-wise minimum of same coordinate (x,y (or x,y,z)) in the simulated CEUS data (FIG. 4) and the dilated data (FIG. 10). As described herein, for this step, a value of the coordinate (x,y) is a minimum of the values of that coordinate (x,y) from the received residual and dilated data. That is, for a given coordinate (x,y), where at least one of the value of the CEUS data or the value of the dilated data is black, the coordinate (x,y) is set to black, and where both the value of the CEUS data and the value of the dilated data is not black (e.g., white or gray in this example), the coordinate (x,y) is set to white or gray. As shown, the circular structures 402, 404, 406, 408, 410 and 412 are all returned to the original radii and the structures 402, 404, 408 and 410 remain without their centroids.

Figure 12:
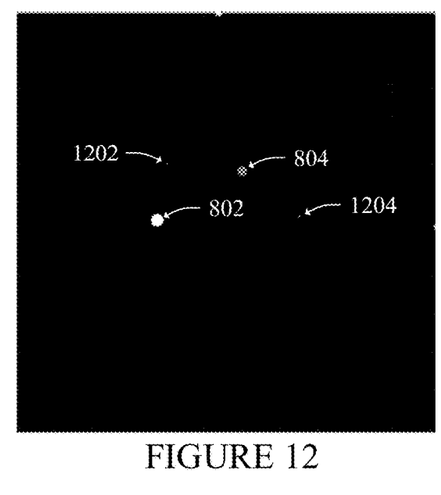
FIG. 12 graphically illustrates microbubble data (markers locating candidate microbubbles), in accordance with an embodiment(s) described herein.

FIG. 12 shows microbubble data created by calculating the arithmetic difference between each coordinate (x,y, or x,y,z) in the CEUS data (FIG. 4) and the minimum value data (FIG. 11). As shown, only the centroids 802, 804, 1202 and 1204 remain. Generally, since the size of the structures in the CEUS data (FIG. 4) and the minimum value data (FIG. 11) is approximately the same, with the only difference being the structures 402, 404, 408 and 410 in the minimum value data do not have their centroids, the difference between this data yields the centroids of the structures 402, 404, 408 and 410 as the markers 802, 804, 1202 and 1204. Again, the markers 802, 804, 1202 and 1204 indicate the position of the microbubbles of interest.

As described herein, the output microbubble data includes all the makers from the microbubble data generated in FIG. 8 and all the makers from the microbubble data generated in FIG. 12. From FIGS. 8 and 12, different microbubble detection structuring elements yield different microbubble data. For example, FIG. 12 includes four markers whereas FIG. 8 yields two markers for the same input simulated CEUS data. That is, the microbubble data of FIG. 12 include the two markers from FIG. 8 (although a different size) and two additional markers. Prior to combining the markers from the two sets of microbubble data, each set can be processed to remove artifact as described herein.

One example application of the approach described herein includes identifying tumors. In general, a tumor has more vasculature than normal tissue. As such, there will be a greater concentration of microbubbles at a tumor cite relative to the surrounding tissue of an organ. The approach described herein improves the detection of such microbubbles and hence improves tumor detection. Another example application of the approach described herein includes determining if a tumor treatment is successful. Again, a tumor has more vasculature than normal tissue. As such, a reduced concentration of microbubbles at a treated tumor cite may indicate the treatment was successful, whereas a same or greater concentration may indicate the treatment was not successful. The approach described herein improves the detection of such microbubbles and hence improves the evaluation of a tumor treatment.

Figure 13:
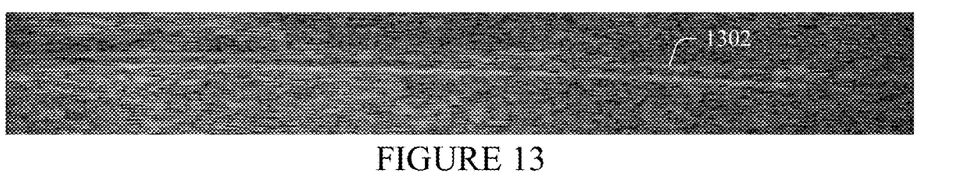
FIG. 13 graphically illustrates an example B-mode image including a portion of a vessel, in accordance with an embodiment(s) described herein.
Figure 14:
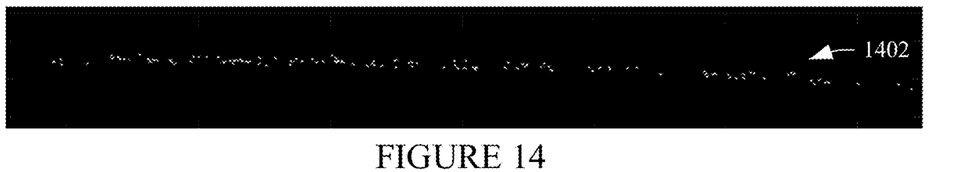
FIG. 14 graphically illustrates a microbubble image with a plurality of microbubble markers for the portion of the vessel, in accordance with an embodiment(s) described herein.
Figure 15:
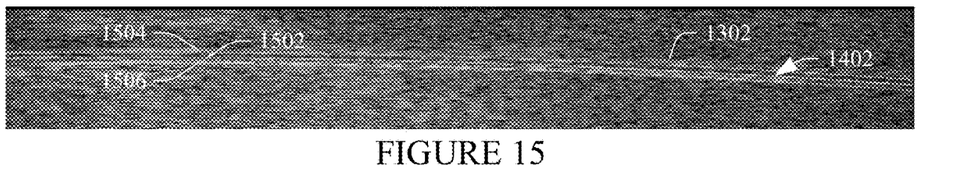
FIG. 15 graphically illustrates the microbubble image superimposed over the B-mode image, in accordance with an embodiment(s) described herein.

Alternatively, or additionally, the microbubble data is used to enhance or segment vasculature. An example is shown in connection with FIGS. 13, 14, 15, 16 and 17. FIG. 13 shows a B-mode image (from tissue data) including a portion of a 200 micro meter vessel 1302. FIG. 14 shows a microbubble image (from CEUS data) with a plurality of microbubble markers 1402 for the portion of the vessel 1302 of FIG. 13. FIG. 15 shows the microbubbles from the microbubble image of FIG. 14 superimposed over the B-mode image of FIG. 13. The line 1502 shows the centroid on all the detected bubbles in the vessel, and the two lines 1504 and 1506 are the candidate vessel boundaries calculated from to be the 95% confidence intervals of the centroid line 1502. The lines 1504 and 1506 in a sense delineate the vessel boundaries. They can also be used to generate a map for compensating for gains inside the vessel.

Figure 16:
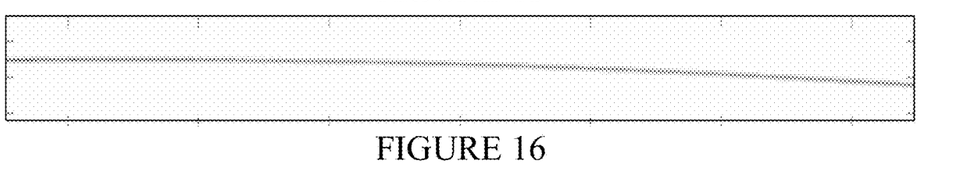
FIG. 16 graphically illustrates a binary mask generated from boundaries of the vessel, in accordance with an embodiment(s) described herein.
Figure 17:
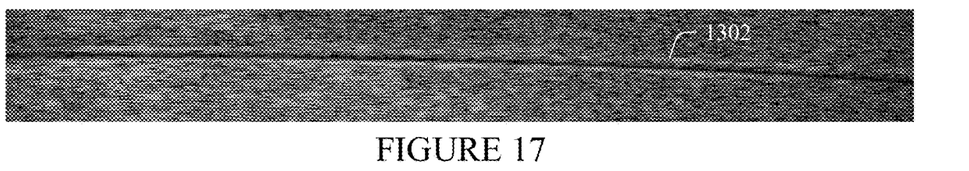
FIG. 17 graphically illustrates the B-mode image with the vessel visually enhanced using the binary mask, in accordance with an embodiment(s) described herein.

FIG. 16 shows a Euclidian distance transform map generated from a mask including the boundaries (1504 and 1506) of the vessel 1302 in the superposition image of FIG. 15. FIG. 17 shows the B-mode image with the vessel 1302 visually enhanced or segmented, relative to the vessel 1302 in FIG. 13, using the map of FIG. 16. In this example, the map is utilized to improve boundary wall delineation relative to other tissue and compensate for gain inside of the vessel 1302.

Figure 18:
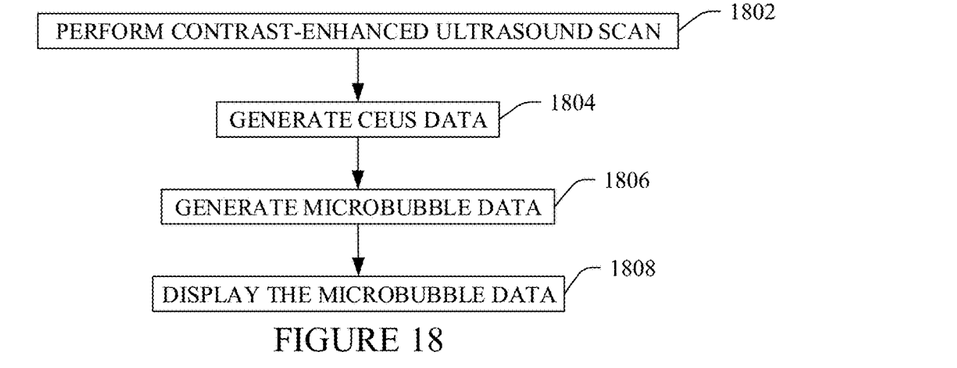
FIG. 18 illustrates an example method in accordance with an embodiment herein.

FIG. 18 illustrates an example method in accordance with an embodiment herein.

The ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 1802, a contrast-enhanced ultrasound scan (using a microbubble-based contrast agent) is performed, as described herein and/or otherwise.

At 1804, at least CEUS data is generated, as described herein and/or otherwise.

At 1806, the CEUS data is processed generate microbubble envelope data, as described herein and/or otherwise.

At 1808, the microbubble envelope data is displayed, as described herein and/or otherwise.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium (which is not computer readable storage medium).

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array configured to transmit an ultrasound pressure field and receive an echo pressure field for a contrast-enhanced scan, and generate an electrical signal indicative of the received echo pressure field;
   a signal processor configured to process the electrical signal and generate at least contrast enhanced ultrasound (CEUS) data indicative of nonlinear signal in the electrical signal;
   a microbubble processor configured to process the CEUS data and generate microbubble data based on a predetermined contrast-agent microbubble size, shape and adjacency for microbubbles of interest,
   wherein the microbubble processor further includes a first structuring element having a first size and a first adjacency and is further configured to apply the first structuring element to the CEUS data to determine first microbubble data based on the first size and the first adjacency; and
   a display configured to display a microbubble image indicative of the microbubble data.

2. The ultrasound imaging system of claim 1, wherein the microbubble data is the first microbubble data.

3. The ultrasound imaging system of claim 1, wherein the microbubble processor further includes a second structuring element having a second size and a second adjacency and is further configured to apply the second structuring element to the CEUS data to determine second microbubble data based on the second size and the second adjacency and to combine the first and second microbubble data to determine the microbubble data.

4. The ultrasound imaging system of claim 3, wherein microbubble processor is further configured to combine the first and second microbubble data to produce the microbubble data.

5. The ultrasound imaging system of claim 4, wherein microbubble processor is further configured to combine the first and second microbubble data through the mathematical union operator.

6. The ultrasound imaging system of claim 4, wherein the microbubble processor is further configured to:
   determine first dilated data by applying the first structuring element to the CEUS data, which removes a bright spot in the center of a structure in the CEUS data only in response to the structure satisfying the first size and the first adjacency and dilates all structures of the CEUS data, creating a ring structure for a structure satisfying the first size and the first adjacency and a disc structure for structure not satisfying the first size and the first adjacency;
   determine first minimum value data by taking a point-wise minimum between the CEUS data and the first dilated data; and
   determine first marker data by calculating an arithmetic difference between the first minimum value data and the CEUS data.

7. The ultrasound imaging system of claim 6, wherein the microbubble processor is further configured to:
   output the first marker data as the first microbubble data.

8. The ultrasound imaging system of claim 6, wherein the microbubble processor is further configured to:
   remove artifact from the first marker data; and
   output the first artifact removed marker data as the first microbubble data.

9. The ultrasound imaging system of claim 8, wherein the microbubble processor is further configured to:
   determine first eroded data by eroding all structures of the first marker data with an artifact removal structuring element having a predetermined size, wherein the predetermined size is less than the first size; and
   determine the first artifact removed marker data by dilating the first eroded data with the artifact removal structuring element.

10. The ultrasound imaging system of claim 4, wherein the signal processor is further configured to process the electrical signal and generate tissue data indicative of linear signal in the electrical signal, and the display is further configured to display a tissue image indicative of the tissue data.

11. The ultrasound imaging system of claim 10, wherein the display is configured to display the microbubble image and the tissue image individually, side-by-size, or one superimposed over the other.

12. The ultrasound imaging system of claim 10, wherein the display is further configured to persist the microbubble data over a predetermined time period.

13. The ultrasound imaging system of claim 10, wherein the display is further configured to display the microbubble data in real-time.

14. A method, comprising:
   acquiring an echo pressure field;
   generating an electrical signal indicative of the acquired echo pressure field;
   processing the electrical signal to generate at least contrast enhanced ultrasound (CEUS) data; and
   processing the CEUS data with a structuring element having a first size and a first adjacency to generate microbubble data based on the first size and the first adjacency.

15. The method of claim 14, further comprising:
   displaying a microbubble image indicative of the microbubble data.

16. The method of claim 14, further comprising:
   processing the electrical signal to generate tissue data; and
   visually enhancing the tissue data based on the microbubble data.

17. A computer-readable storage medium storing instructions that when executed by a computer cause the computer to:
   acquire an echo pressure field;
   generate an electrical signal indicative of the acquired echo pressure field;
   process the electrical signal to generate at least contrast enhanced ultrasound (CEUS) envelope data; and
   process the CEUS data with a structuring element having a first size and a first adjacency to generate microbubble data based on the first size and the first adjacency.

18. The computer-readable storage medium of claim 17, wherein the instructions further cause the processor to:
   display a microbubble image indicative of the microbubble data.

19. The computer-readable storage medium of claim 17, wherein the instructions further cause the processor to:
   process the electrical signal to generate tissue data; and
   visually enhance the tissue data based on the microbubble data.

* * * * *